United States Patent
Sramek

(10) Patent No.: US 9,642,747 B2
(45) Date of Patent: *May 9, 2017

(54) ENDPOINT-MANAGED PHOTOCOAGULATION

(71) Applicant: Topcon Medical Laser Systems, Inc., Santa Clara, CA (US)

(72) Inventor: Chris Sramek, Sunnyvale, CA (US)

(73) Assignee: TOPCON MEDICAL LASER SYSTEMS, INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/823,864

(22) Filed: Aug. 11, 2015

(65) Prior Publication Data

US 2016/0100984 A1  Apr. 14, 2016

Related U.S. Application Data

(63) Continuation of application No. 13/278,066, filed on Oct. 20, 2011, now Pat. No. 9,101,447.

(51) Int. Cl.
  *A61B 18/20* (2006.01)
  *A61F 9/008* (2006.01)
(52) U.S. Cl.
  CPC ...... *A61F 9/00821* (2013.01); *A61F 2009/00855* (2013.01); *A61F 2009/00863* (2013.01)
(58) Field of Classification Search
  CPC .. A61F 9/008; A61F 9/00802; A61F 9/00821; A61F 2009/00861; A61F 2009/00863; A61F 2009/00872; A61F 2009/00878; A61F 2009/00885; A61F 2009/00897; A61B 18/18; A61B 18/20
  (Continued)

(56) References Cited

U.S. PATENT DOCUMENTS

| 8,074,661 B2 | 12/2011 | Hutson et al. |
| 8,496,650 B2 * | 7/2013 | Sramek ............... A61F 9/008 606/13 |

(Continued)

FOREIGN PATENT DOCUMENTS

| EP | 1872754 A1 | 1/2008 |
| JP | 5133069 B2 | 1/2013 |

OTHER PUBLICATIONS

International Search Report and Written Opinion received for PCT Patent Application No. PCT/US2012/61178, mailed on Jan. 7, 2013, 7 pages.

(Continued)

*Primary Examiner* — Ahmed Farah
(74) *Attorney, Agent, or Firm* — Morrison and Foerster, LLP

(57) ABSTRACT

Systems and processes are described relating to laser-based ophthalmic intervention technologies and, more specifically, to techniques for delivering reproducible amounts of laser energy to create visible and sub-visible lesions on an eye. The subject technology may provide a user with the ability to adjust the amount of energy to be delivered to the eye tissue by selecting a single numerical value. In response, the system may adjust the power and/or duration of the laser treatment beam pulse according to an operating curve determined by the system.

30 Claims, 6 Drawing Sheets

(58) Field of Classification Search
USPC .............................. 606/4–6, 10–12; 128/898
See application file for complete search history.

(56) References Cited

U.S. PATENT DOCUMENTS

| | | | |
|---|---|---|---|
| 9,005,261 B2* | 4/2015 | Brinkmann | A61F 9/008 372/1 |
| 9,101,447 B2* | 8/2015 | Sramek | A61F 9/00821 |
| 2003/0179344 A1 | 9/2003 | Van de Velde | |
| 2004/0098070 A1* | 5/2004 | Mohr | A61B 18/20 607/89 |
| 2005/0224460 A1 | 10/2005 | Hutson et al. | |
| 2006/0187978 A1 | 8/2006 | Telfair et al. | |
| 2009/0112195 A1 | 4/2009 | Zemmouri | |
| 2009/0275929 A1* | 11/2009 | Zickler | A61B 3/113 606/5 |
| 2010/0049180 A1 | 2/2010 | Wells et al. | |
| 2010/0168724 A1 | 7/2010 | Sramek et al. | |
| 2010/0292763 A1* | 11/2010 | Brinkmann | A61F 9/00821 607/89 |
| 2013/0204235 A1* | 8/2013 | Palanker | A61F 9/008 606/4 |
| 2016/0058617 A1* | 3/2016 | Luttrull | A61F 9/00821 606/5 |

OTHER PUBLICATIONS

International Preliminary Report on Patentability received for PCT Patent Application No. PCT/US2012/061178, mailed on May 1, 2014, 6 pages.

Extended European Search Report (includes Supplementary European Search Report and Search Opinion) received for European Patent Application No. 12842594.9, mailed on May 15, 2015, 7 pages.

Final Office Action received for U.S. Appl. No. 13/278,066 mailed on Oct. 2, 2014, 5 pages.

Non Final Office Action received for U.S. Appl. No. 13/278,066, mailed on Dec. 6, 2013, 11 pages.

Non-Final Office Action received for U.S. Appl. No. 13/278,066, mailed on Jun. 20, 2014, 6 pages.

Notice of Allowance received for U.S. Appl. No. 13/278,066, mailed on Apr. 6, 2015, 5 pages.

Notice of Allowance received for U.S. Appl. No. 13/278,066, mailed on Dec. 10, 2014, 5 pages.

Banerjee et al., "Influence of Laser Parameters on Selective Retinal Treatment Using Single-Phase Heat Transfer Analyses", Medical Physics, vol. 34, No. 5, May 2007, pp. 1828-1841.

Figueira et al., "Prospective Randomized Controlled Trial Comparing Sub-threshold Micropulse Diode Laser Photocoagulation and Conventional Green Laser for Clinically Significant Diabetic Macular Oedema", Br. J. Ophthalmol. vol. 93, No. 10, 2009, pp. 1341-1344.

Laursen et al., "Subthreshold Micropulse Diode Laser Treatment in Diabetic Macular Oedema", Br J Ophthalmol, vol. 88, 2004, pp. 1173-1179.

Lavinsky et al., "Randomized Clinical Trial Evaluating mETDRS Versus Normal or High-Density Micropulse Photocoagulation for Diabetic Macular Edema", Investigative Ophthalmology & Visual Science, vol. 52, No. 7, Jun. 2011, pp. 4314-4323.

Ohkoshi et al., "Subthreshold Micropulse Diode Laser Photocoagulation for Diabetic Macular Edema in Japanese Patients", American Journal of Ophthalmology, vol. 149, No. 1, 2010, pp. 133-139.

Parodi et al., "Intravitreal Triamcinolone Acetonide Combined with Subthreshold Grid Laser Treatment for Macular Oedema in Branch Retinal Vein Occlusion: A Pilot Study", Br J Ophthalmol. vol. 92, No. 8, Aug. 2008, pp. 1046-1050.

Office Action received for Australian Patent Application No. 2012325863, mailed on Jun. 7, 2016, 2 pages.

Office Action received for Japanese Patent Application No. 2014-537331, mailed on Jul. 25, 2016, 3 pages (2 pages of Official copy and 1 page of English translation).

* cited by examiner

ENDPOINT-MANAGED PHOTOCOAGULATION

CROSS-REFERENCE TO RELATED APPLICATON

This application is a continuation of U.S. application Ser. No. 13/278,066 filed on Oct. 20, 2011 (now U.S. Pat. No. 9,101,447), the content of which is incorporated herein by reference in its entirety for all purposes.

BACKGROUND

1. Field

The present disclosure relates to laser-based ophthalmic intervention technologies and, more specifically, to delivering laser energy to create reproducible visible and sub-visible lesions on an eye.

2. Related Art

Every year, thousands of patients in the United States and other countries undergo laser-based interventional treatments of the eye. Such treatments typically involve the application of laser energy in the form of a laser treatment beam having a controlled power and controlled duration to targeted tissue structures to create visible or sub-visible lesions (also referred to herein as "endpoints"). These treatments may be used to address clinical problems, such as diabetic retinopathy, diabetic macular edema, age-related macular degeneration, glaucoma, or the like.

The power and duration required to produce the visible or sub-visible lesions of the desired endpoint may vary from patient to patient due to varying tissue pigmentation. To account for this, clinicians may typically start the treatment by applying a laser treatment beam having a standard power and duration for a particular type of endpoint. Based on the observed endpoint, the clinician may titrate the power and/or duration of the laser treatment beam until a desired endpoint is created. For example, a clinician may apply a laser treatment beam having a particular power and duration in an attempt to produce a barely-visible lesion. However, the laser treatment beam may instead produce a sub-visible lesion. In response, the clinician may increase the power and/or duration by an amount determined by the clinician based on previous experience. The laser treatment beam may again be applied to the patient's eye using the increased power and/or duration settings and the resulting endpoint may be observed. This process may be repeated until a barely-visible lesion is produced.

One inherent drawback to this approach is that there is little uniformity between clinicians in the way they titrate the power and duration of the laser treatment beam due to the subjective nature of visually assessing the lesion grade. Additionally, clinicians often over-adjust the laser treatment beam due to the non-linear relationship between power/duration and the tissue response induced by the laser treatment beam.

Another drawback is that while this technique can be used to produce a desired visible endpoint, the lack of immediate feedback makes this method insufficient for producing sub-visible endpoints. When a sub-visible endpoint is desired, some clinicians titrate to a visible endpoint and then adjust the power and duration of the applied laser pulse using heuristically generated algorithms to achieve their endpoint. Such algorithms generally titrate with continuous wave 50-300 ms (CW) pulses and (1) adjust power by a multiple in the 0.5-2× range, (2) switch to a micropulsed regime (2 ms pulse envelope) with a 5-15% duty cycle, and (3) adjust the overall micropulse burst length (50-2000 ms). These and other titration algorithms are described in J Figueira, J Khan, S Nunes, et al. "Prospective Randomized Controlled Trial Comparing Sub-threshold Micropulse Diode Laser Photocoagulation and Conventional Green Laser for Clinically Significant Diabetic Macular Oedema." Br J Ophthalmol (2009); 93: 1341-1344, Laursen M L, Moeller F, Sander B, Sjoelie A K. "Subthreshold Micropulse Diode Laser Treatment in Diabetic Macular Oedema." Br J Ophthalmol 2004; 88:1173-1179, Ohkoshi K, Yamaguchi T. "Subthreshold Micropulse Diode Laser Photocoagulation for Diabetic Macular Edema in Japanese Patients." Am J Ophthalmol 2010; 149:133-139, Parodi M B, Iacono P, Ravalico G. "Intravitreal Triamcinolone Acetonide Combined with Sub-threshold Grid Laser Treatment for Macular Oedema in Branch Retinal Vein Occlusion: A Pilot Study." Br J Ophthalmol 2008; 92: 1046-1050, and Lavinsky, D., et al. "Randomized Clinical Trial Evaluating mETDRS Versus Normal or High-Density Micropulse Photocoagulation for Diabetic Macular Edema." Invest Ophthalmol Vis Sci (2011); 52(7): 4314-23. Unfortunately, due to the clinician-to-clinician variation in titration and the non-linear relationship between power/duration and tissue response, these results are difficult to replicate from one clinician to another.

Thus, a standard and reproducible process for producing visible and sub-visible lesions is desired.

SUMMARY

Systems for delivering reproducible amounts of laser energy to create visible and sub-visible lesions on an eye are provided. The systems may provide a user with the ability to adjust the amount of energy delivered to the eye tissue by selecting a single numerical value. In response, the system may adjust the power and/or duration of the laser treatment beam pulse according to an operating curve determined by the system.

Generating the operating curve may include determining a constant Arrhenius integral value associated with the power and the duration of the laser treatment beam pulse, plotting a constant-Arrhenius curve having the constant Arrhenius integral value, plotting a plurality of constant-Arrhenius curves having logarithmic values of the constant Arrhenius integral value, assigning a maximum energy value of an energy value scale to the power and the duration that causes the detectable lesion, and generating the operating curve based at least in part on a plurality of intersection points between energy values of the energy value scale and the plurality of constant-Arrhenius curves and an intersection point between the maximum energy value of the energy value scale and the constant Arrhenius curve.

Processes for delivering reproducible amounts of laser energy are also provided.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the present technology. Thus, the disclosed technology is not intended to be limited to the examples described herein and shown, but is to be accorded the scope consistent with the claims.

As described above, laser-treatment systems are commonly used to deliver laser energy to targeted portions of the eye in order to create lesions or increase the temperature of the eye at desired locations. The embodiments described herein may provide a user with the ability to adjust the amount of energy delivered to the eye tissue by selecting a single numerical value. In response, the disclosed laser-treatment system may adjust the power and/or duration of the laser treatment beam according to an operating curve determined by the system.

Figure 1:
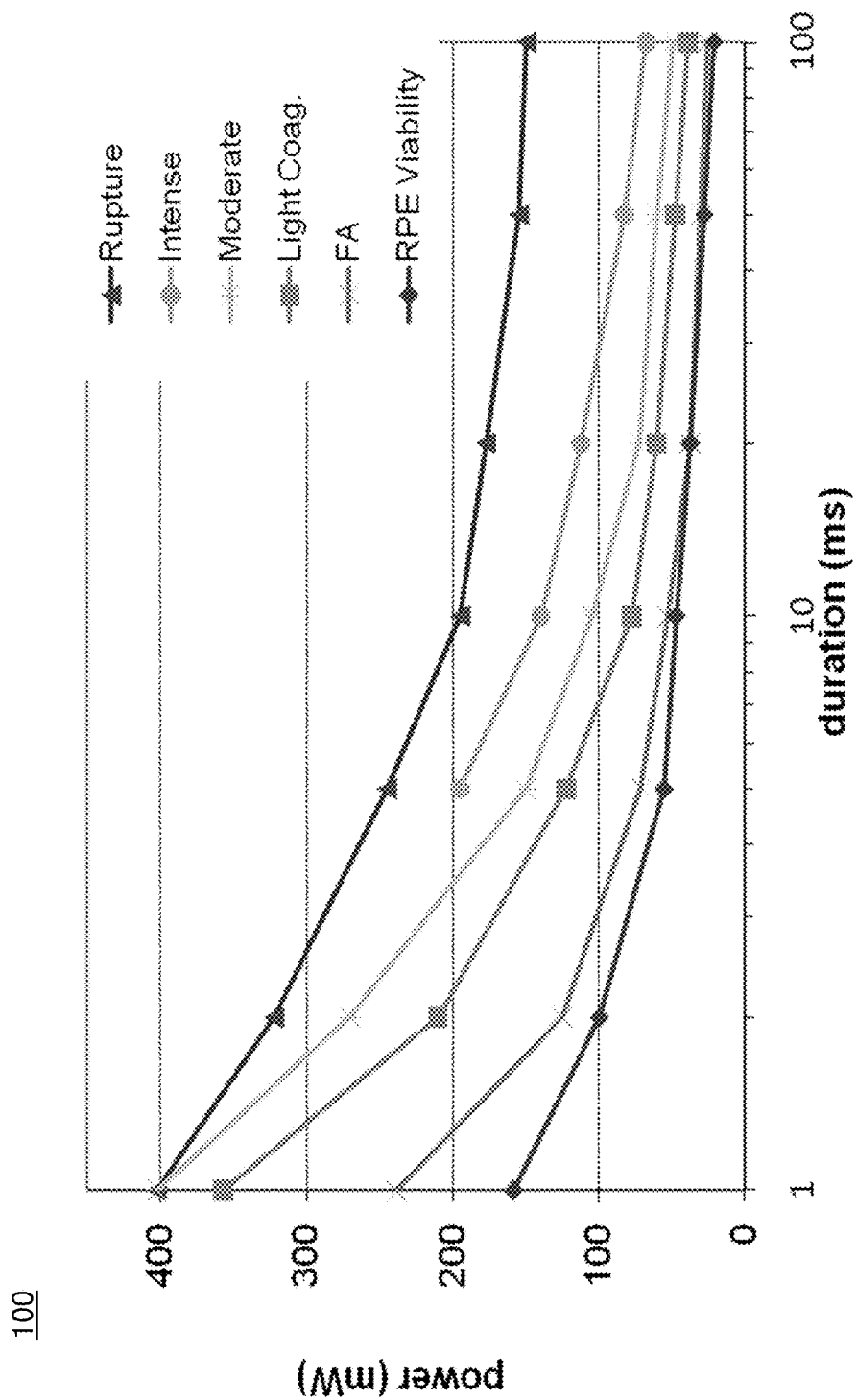
FIG. 1 illustrates a graph showing average power and treatment duration thresholds for generating various endpoint types.

FIG. 1 includes a graph 100 showing average power and laser treatment beam duration thresholds (points at which each type of endpoint becomes noticeable) for generating various endpoint types. Specifically, threshold power and duration values for rupture, intense burn, moderate burn, light coagulation, fluorescein angiography (FA), and retinal pigment epithelium (RPE) damage type endpoints are shown. For clarity purposes, the duration (x-axis) is shown on a logarithmic scale while the power (y-axis) is shown on a linear scale.

As can be seen in FIG. 1, the type of endpoint produced by the applied laser treatment beam can be changed by adjusting the power of the laser treatment beam, the duration that the laser treatment beam is applied, or a combination of power and duration. Thus, conventional laser-based treatment systems typically include controls allowing the operator to independently adjust both the power of the laser treatment beam and the duration of each laser treatment beam pulse. However, controlling the type of endpoint generated in this manner can be difficult.

Figure 2:
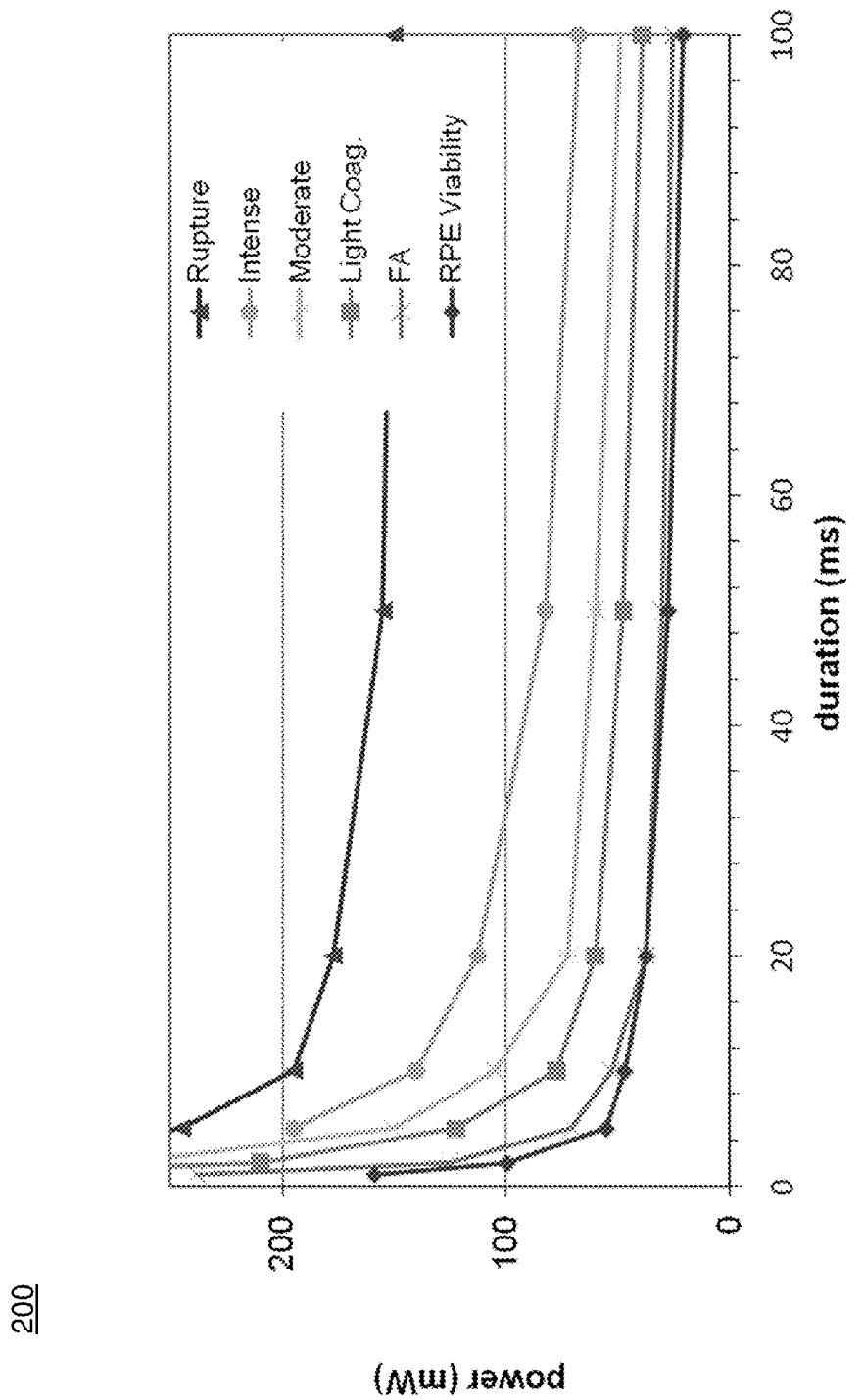
FIG. 2 illustrates another graph showing average power and treatment duration thresholds for generating various endpoint types.

To illustrate, FIG. 2 includes a graph 200 showing average power and treatment duration thresholds for generating various endpoint types. Graph 200 is similar to graph 100, except that both the duration (x-axis) and power (y-axis) are shown on a linear scale.

As mentioned above, the endpoint type can be changed by adjusting the power of the laser treatment beam, the duration that the laser treatment beam is applied, or a combination of power and duration. However, as shown in FIG. 2, adjusting only the power of the laser treatment beam can yield inconsistent results. In particular, depending on the duration of the laser treatment beam, small changes in power can result in drastic changes in the type of endpoint created or large changes in power can result in little to no change in the type of endpoint created. For example, a laser treatment beam having a duration of 80 ms and a power of approximately 50 mW may produce a moderate burn type endpoint. If the clinician is attempting to produce an RPE damage type endpoint, the clinician may choose to decrease the power of the laser treatment beam pulse while keeping the duration constant. To generate the desired RPE damage type endpoint, the clinician may be required to decrease the power to approximately 20 mW. Thus, this relatively small decrease in power (30 mW) may change the endpoint type from a moderate burn type endpoint to an RPE damage type endpoint. However, if a laser treatment beam having a shorter duration is used, larger changes in power may be required to change the endpoint type. For example, a laser treatment beam having a duration of 8 ms and a power of 125 mW may produce a moderate burn type endpoint. To produce the desired RPE damage type endpoint, the clinician may be required to decrease the power to approximately 60 mW. Thus, a decrease of about 65 mW may be required to change the endpoint type from a moderate burn type endpoint to an RPE damage type endpoint. This decrease in power is significantly larger than the 30 mW decrease required for an 80 ms duration laser treatment beam pulse. As a result, it can be difficult for a clinician to predictably change the endpoint type by adjusting only the power of the laser treatment beam pulse. Moreover, precise control over the power may be required due to the relatively small differences in power required to generate the different endpoint types.

Adjustment of only the duration of the laser treatment beam pulse to control the type of endpoint produced may similarly yield inconsistent results. In particular, depending on the type of endpoint generated and the type of endpoint desired, small changes in duration can result in drastic changes in the type of endpoint created or large changes in duration can result in little to no change in the type of endpoint created. For example, a laser treatment beam having a power of 100 mW and a duration of 100 ms may produce an intense burn endpoint. If the clinician is attempting to produce a moderate burn type endpoint, the clinician may choose to reduce the duration of the laser treatment beam while keeping the power constant. To generate the desired moderate burn, the clinician may be required to decrease the duration to approximately 32 ms. Thus, this relatively large decrease in duration (68 ms) may be required to change the endpoint type from an intense burn endpoint to a moderate burn endpoint. However, if a laser treatment beam having a power of 100 mW and a duration of 6 ms is used, a FA type endpoint may be generated. If the clinician is attempting to produce an RPE damage type endpoint, the clinician may choose to reduce the duration of the laser treatment beam pulse while keeping the power constant. To generate the desired RPE damage type endpoint, the duration may be decreased to between approximately 2 ms and 4 ms. This change in laser treatment beam pulse duration is significantly smaller than the 68 ms change required to change the laser treatment beam pulse from an intense burn type endpoint to a moderate burn type endpoint. As a result, it can be difficult for a clinician to predictably change the endpoint type by adjusting only the duration of the laser treatment beam.

As can be seen from the examples described above, it can be difficult for a clinician to control the endpoint type by adjusting only the power or by adjusting only the duration of the laser treatment beam pulse since there is no linear relationship between the amount of change (in power or duration) and the resulting endpoint type. Manually adjusting both the power and the duration simultaneously can lead to even more difficulty in generating a desired type of endpoint. To add to this unpredictability, the absolute value of the endpoint threshold power at each pulse duration can vary from patient to patient due to variations in pigmentation, though their relative values are constant or at least substantially constant.

Thus, in some embodiments, a laser-treatment system is provided that allows the clinician or operator of the system to adjust the parameters of the laser treatment beam by selecting a single, linear value. The system may then adjust the power and duration of the laser treatment beam pulse in response to the selected linear value. In some embodiments, the linear value can be expressed as a percentage (e.g., 0%-100%). However, it should be appreciated that any linear numerical scale can be used. In this way, the clinician can intuitively adjust the parameters of the laser treatment beam pulse to change by a desired amount. For example, a change from 20% to 40% may result in a similar change in energy delivered as a change from 60% to 80%. This can reduce or eliminate the confusion related to the adjustment of the power and duration of the laser treatment beam described above.

Figure 3:
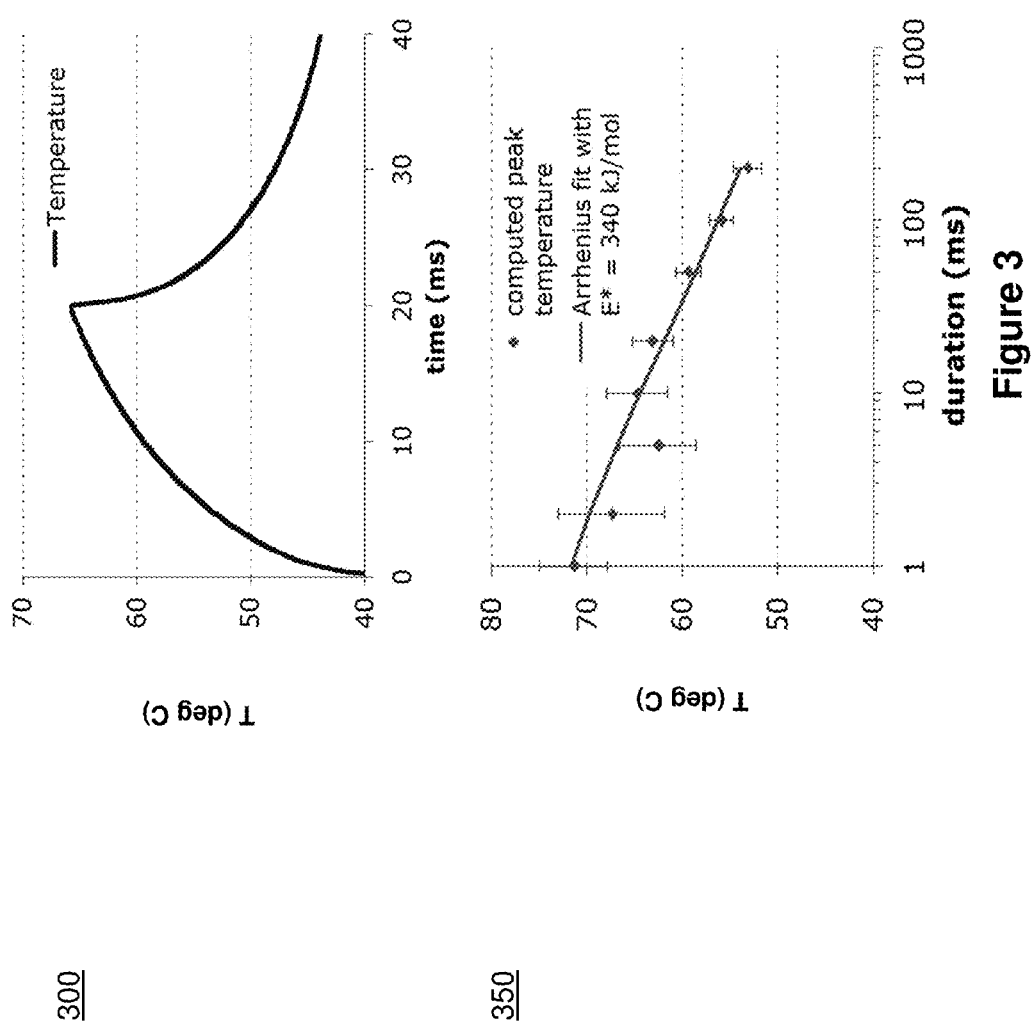
FIG. 3 illustrates a graph showing peak tissue temperatures caused by laser treatment beams of varying durations.

To generate the described linear scale, the endpoint produced for a given laser treatment beam power and duration may be modeled computationally. Generally, the type of endpoint created depends on the level of cellular thermal response to heating by the laser treatment beam. Thus, the endpoint generated by a particular power and duration can be quantified using a value representative of the cellular response to the laser treatment beam. Tissue thermal coagulation (protein denaturation) caused by a laser treatment beam is an Arrhenius-law process. The Arrhenius model of cellular damage is based on the assumptions of (1) the existence of a critical component of cellular metabolism (protein) with lowest thermal tolerance, (2) a description of the denaturation of this component in terms of chemical reaction theory, and (3) an absence of cellular repair during the period of hyperthermia. In this model, the coagulation rate is an exponential function with respect to temperature (expressed as equation 1.1 below). Specifically, equation 1.1 shows that the rate of change in concentration of the critical protein species at a given time (dC(t)) is a function of the total non-denatured concentration (C(t)) at that time multiplied by an exponential function ($\exp([-E^*/(R-T(t))])$), where R is the universal gas constant, $E^*$ is the activation energy for the particular protein (to be discussed in greater detail below with respect to FIG. 3), A is a rate constant, and T(t) is the temperature of the targeted tissue as a function of time.

$$dC(t) = A \cdot C(t) \exp\left(\frac{-E^*}{R \cdot T(t)}\right) dt \quad 1.1$$

Thus, to estimate the overall reduction in the protein's concentration caused by a laser treatment beam inducing temperature profile T(t) (both heating and cooling phases), a cellular damage model, such as a cellular damage model based on an Arrhenius-type equation, can be used. For example, the Arrhenius integral shown in equation 1.2 can be calculated, where $C_{th}$ is the unaffected protein concentration and $C_O$ is the initial concentration. The protein concentration decreases by $e^{(-\Omega)}$ during the on time of the laser treatment beam. While a specific example equation is provided below for equation 1.2, it should be appreciated by those of ordinary skill in the art that other equations can be used.

$$\Omega = -\ln\left(\frac{C_{th}}{C_0}\right) = A \int \exp\left(\frac{-E^*}{R \cdot T(t)}\right) dt \quad 1.2$$

The criterion for cell viability is the maximum tolerable decrease in this critical component, usually assumed to be 1. While reports have claimed that cells may not survive with even 5-10% of a key protein denatured, selection of this value may affect the value of the rate constant A determined from cell viability experimental data, but not the value of $E^*$. Values below 1 indicate that the power and duration from the laser exposure was nominally sub-lethal, but did result in some level of coagulation, which may or may not correspond to a detectable endpoint. With the Arrhenius model of coagulation, power/duration combinations resulting in the same Arrhenius integral are presumed to correspond to the same visible or sub-visible endpoint.

To determine the activation energy $E^*$ described above, the tissue temperature caused by a laser treatment beam may be computed using known computational models of tissue heating at various treatment beam durations given the parameters of the laser treatment beam (e.g., power, spot size, and the like) and the targeted tissue. For example, FIG. 3 includes graph 300 showing the tissue temperature as a function of time when a laser treatment beam is applied for 20 ms. As shown in graph 300, the temperature of the tissue increases to a peak value (approximately 65° C.) at 20 ms, at which time the laser treatment beam is no longer applied. The temperature of the tissue then decreases as heat diffuses from the treated area. The peak tissue temperature may be calculated for various laser treatment beam durations and powers corresponding to the same endpoint and the results may be plotted as shown in graph 350. Using the computed temperature time-courses (T(t) in equation 1.2), an Arrhenius fit may be generated, with the fit representing the activation energy $E^*$ for the particular tissue or protein. This determined activation energy $E^*$ value may then be used in equations 1.1 and 1.2 shown above. While specific values are provided above, it should be appreciated that other values may be used depending on the computational model used for estimating the temperature time-course (or physical measurements of temperature in tissue) for the targeted tissue.

Figure 4:
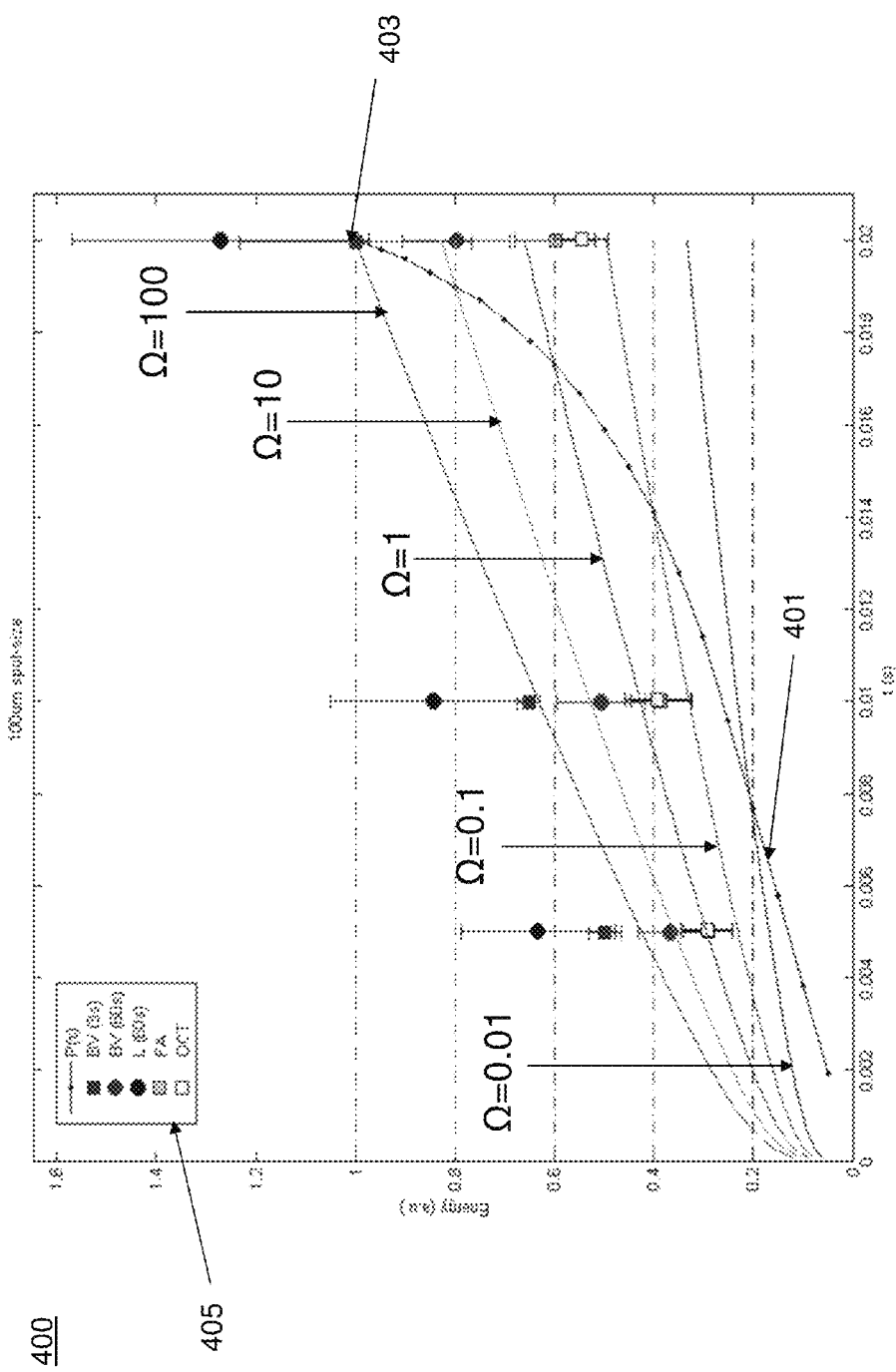
FIG. 4 illustrates an operating curve for visible or sub-visible endpoint delivery.

Using equation 1.2 shown above, a relationship between a linear scale and exponential changes in Arrhenius integral values can be established. For example, FIG. 4 includes graph 400 showing the calculated constant-Arrhenius curves (labeled $\Omega=0.01$, $\Omega=0.1$, $\Omega=1$, $\Omega=10$, $\Omega=100$), experimentally measured threshold energies for producing various endpoint types, and an operating curve 401. The linear scale representing the normalized energy (power multiplied by pulse duration) of the laser treatment beam pulse is shown on the y-axis and the duration of the laser treatment beam pulse is shown on the x-axis. Treatments resulting in the same Arrhenius integral produce the same endpoint type. Thus, energy-duration combinations along a particular constant-Arrhenius curve (e.g., $\Omega=0.01$, $\Omega=0.1$, $\Omega=1$, $\Omega=10$, $\Omega=100$) may produce the same endpoint type. As shown in FIG. 4, the slope of the experimentally measured threshold energies (points on the graph identified by the symbols in key 405) for producing various endpoint types closely matches the slope of the calculated constant-Arrhenius curves.

Operating curve 401 represents the energy-duration combinations that the system is configured to output for selected normalized energy values shown on the y-axis. To generate operating curve 401, a maximum laser treatment beam duration may be selected by a user. The maximum duration may be selected based on the laser-treatment system capabilities, clinician preferences, laser-treatment system manufacturer recommendations, and the like. Once the maximum duration is selected, the power of the laser treatment beam may be titrated using the maximum laser treatment beam duration (e.g., 20 ms in the example shown in FIG. 4) to a power corresponding to a desired endpoint type (e.g., barely visible endpoint after 3 seconds in the example shown in FIG. 4). The desired endpoint type should be a detectable endpoint, meaning that the endpoint is either visible with the naked eye or visible using a chemical, dye, or other intra-operative imaging technology. The energy value (power multiplied by duration) corresponding to the titrated power and maximum duration can be plotted on energy vs. time graph 400 (shown as point 403). The constant-Arrhenius value (e.g., $\Omega=100$ in the example shown in FIG. 4) corresponding to (intersecting) this energy-duration point 403 may be determined and may be plotted on the graph. Logarithmic scales of the corresponding constant-Arrhenius curve (e.g., $\Omega=0.01$, $\Omega=0.1$, $\Omega=1$, and $\Omega=10$ in the example shown in FIG. 4) may also be plotted on the graph. In some embodiments, once the constant Arrhenius curves are plotted, the energy values on the y-axis of the graph may be changed or normalized to any desired linear scale (e.g., 0-1 in the example shown in FIG. 4). The point 403 on graph 400 corresponding to the energy and duration that generates the desired barely visible endpoint may be assigned the highest linear scale value (e.g., 1 in FIG. 4). Intersections between the different constant-Arrhenius curves and constant energy lines (normalized energy values 0.8, 0.6, 0.4, and 0.2) may then be plotted and operating curve 401 may be fit to these intersection points. Thus, when a user selects a particular normalized energy value, the system may adjust the power and duration of the pulse according to operating curve 401. In this way, linear changes in pulse energy can be tied to exponential changes in Arrhenius integral values.

While the example shown in FIG. 4 shows a normalized operating curve 401 for a barely visible endpoint (barely visible after 3 seconds), normalized operating curves for other types of endpoints maybe generated. In these examples, using the maximum pulse duration, the power may instead by titrated to the desired type of endpoint, such as light coagulation, barely visible after 60 seconds, moderate burn, and the like. Additionally, while operating curve 401 is generated using linear changes in energy (power multiplied by duration) and exponential scales of constant-Arrhenius values, fixed duration and exponential changes in power or fixed power and exponential changes in duration may instead be tied to exponentially scaled changes in Arrhenius integral values and used to generate operating curve 401.

Figure 5:
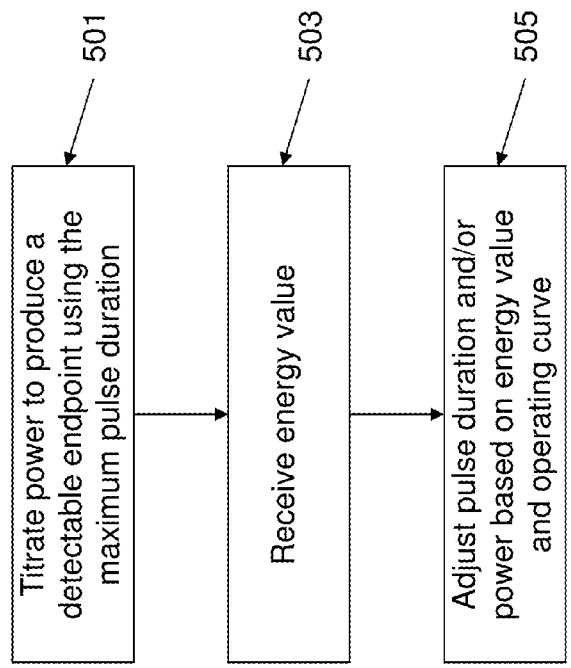
FIG. 5 illustrates an exemplary process for visible or sub-visible endpoint delivery.

FIG. 5 illustrates an exemplary process for visible or sub-visible endpoint delivery using operating curve 401. At block 501, the laser-treatment system may be titrated to produce a detectable endpoint at the maximum laser treatment beam pulse duration. The detectable endpoint may be a visible lesion capable of being seen with the naked eye or may be a sub-visible lesion requiring a chemical, dye, or other intra-operative imaging technology. The maximum desired pulse duration may be selected to be any value and may be selected based on the laser-treatment system capabilities, clinician preferences, laser-treatment system manufacturer recommendations, and the like. Based on the selected maximum pulse duration, the power of the laser treatment beam may be titrated to generate a detectable endpoint and an operating curve may be generated in a manner similar to that described above with respect to FIG. 4. In some embodiments, to generate sub-visible endpoints, the power may be titrated to produce a barely visible lesion and the operating curve may be generated as described above with respect to FIG. 4. In other embodiments, to generate visible endpoints, the power may instead be titrated to produce a visible lesion, such as an intense burn, moderate burn, or light coagulation endpoint, and an operating curve may be generated in a manner similar to that described above with respect to FIG. 4.

At block 503, the laser-treatment system may receive an energy value selected by the system user. The energy value may be selected from a linear scale and may be represented as a percentage or other numerical value. The user may select the energy value based on previous experience, system manufacturer recommendations, published clinical results, and the like. In some embodiments, the laser-treatment system may provide any type of user interface, such as a knob, slider, touch screen, keyboard and display, or any other interface, to allow the clinician to select the energy value.

At block 505, the system may adjust the laser treatment beam duration and/or power based on the selected energy value and the determined operating curve 401. In other embodiments, the laser treatment beam duration may remain constant, while the power may be changed exponentially. In yet other embodiments, the laser treatment beam power may remain constant, while the duration may be changed exponentially.

Figure 6:
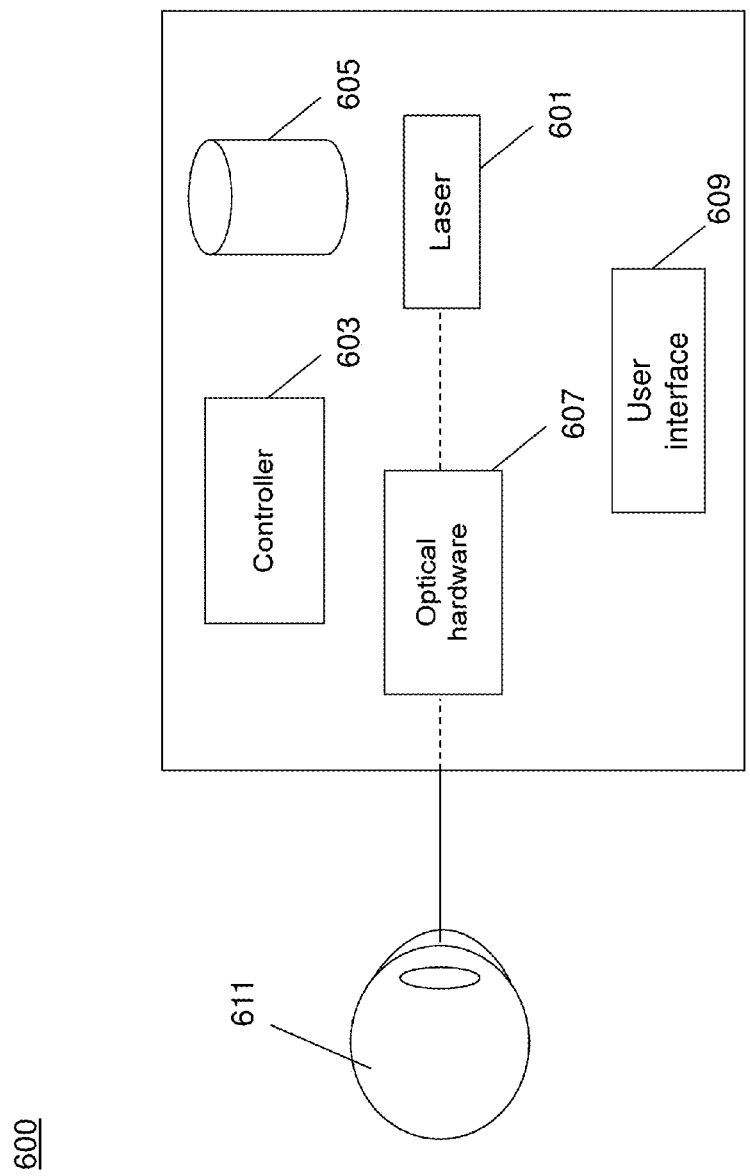
FIG. 6 illustrates an exemplary laser-treatment system for visible or sub-visible endpoint delivery.

FIG. 6 illustrates an exemplary laser-treatment system 600 for delivering laser treatment beams according to various embodiments. System 600 may include laser source 601 configured to transmit a single laser beam. In some embodiments, laser source 601 may include an Argon laser, Krypton laser, diode laser, Nd-YAG laser, or any other pulsed or continuous wave laser suitable for eye therapy. The beam generated by laser source 601 may be continuous or pulsed at a duration from about 1 ms to about 1 second, may have a power from about 30 mW to about 2 W, may have a diameter from about 50 μm to about 500 μm (e.g., about 60 μm or about 400 μm), and may have a wavelength in the visible spectrum (e.g., 532 nm, 561 nm, 577 nm, 647 nm, 659 nm, or 670 nm) or a wavelength in the non-visible spectrum (e.g., 810 nm). However, it should be appreciated that a laser source 601 producing a beam of laser energy having other characteristics may be used.

System 600 may further include optical hardware 607 for manipulating the laser beam generated by laser source 601. In some embodiments, optical hardware 607 may include a spot size selector (not shown) for adjusting the "spot size" of the laser beam delivered to the patient. The "spot size" of a beam refers to the size or diameter of the laser beam. The spot size selector may include continuous magnification change optics, a rotating turret of different magnification optics, or any other arrangement of optics used to change magnification known to those skilled in the art. The spot size selector may be configured to receive the single laser beam from laser source 601 and selectively adjust the size of the single laser beam by varying the selected magnification. The single laser beam may be aimed at the spot size selector, may be directed to spot size selector by an optical fiber, or may be directed to the spot size selector from a free-space laser source with relay or collimating optics.

In some embodiments, optical hardware 607 may further or alternatively include scanning hardware that uses the single laser beam from laser source 601 to generate a single laser beam or a patterned laser beam. In some embodiments, the scanning hardware may include a collimating lens (not shown), first and second scanning devices (not shown), such as galvanometers, MEMS devices, rotating polygons, or the like, and an optional set of relay lenses (not shown) separating the first and second scanning devices. The collimating lens may be configured to receive the laser beam. The output of the collimating lens may be a collimated beam that may be directed to a first scanning device, such as a galvanometer, MEMS device, rotating polygon, or the like. The position of the first scanning device may be precision controlled using a computerized control system (e.g., controller 603) to aim the collimated beam to a second scanning device, such as a second galvanometer, MEMS device, rotating polygon, or the like. The second scanning device may be configured to respond to the computerized control system (e.g., controller 603) to adjust the collimated beam in a direction orthogonal to the direction of adjustment of the first scanning device. In other words, the pair of scanning devices may be utilized to adjust the X-Y Cartesian position of the treatment beam. In some examples, this may be done to move a single treatment beam relative to the patient's eye 611. In other examples, the scanning devices may be synchronized with the pulses generated by the laser source 601 and cycled through several positions relatively quickly to produce a patterning effect. In the depicted system, the beam exiting the optical hardware 607 may be directed to the patient's eye 611. The treatment beam may be delivered to the patient's eye 611 using any known delivery device, such as a slit lamp, head-mounted laser indirect ophthalmoscope, handheld laser endoprobe, or the like.

System 600 may further include controller 603 for controlling laser source 601 (e.g., pulse duration, power, wavelength, etc.) and components of optical hardware 607. Controller 603 may include a general or special purpose processor configured to control the various components of system 600. Controller 603 may further include a non-transitory computer-readable storage medium for providing instructions to the processor for execution. For example, controller 603 may include instructions for performing process 500, described above. Such instructions, generally referred to as "computer program code" (which may be grouped in the form of computer programs or other groupings), when executed, enable the processor to perform features or functions of embodiments of the apparatus and processes described herein. In some examples, the computer-readable storage medium may include a main memory, such as a random access memory (RAM) or other dynamic memory, for storing information and instructions to be executed by a processor. The main memory may also be used for storing temporary variables or other intermediate information during execution of instructions to be executed by the processor. The computer-readable storage medium may likewise include a read-only memory ("ROM") or other static storage device coupled for storing static information and instructions for the processor. In some embodiments, system 600 may further include database 605 for storing instructions for controller 603, settings for laser source 601, and/or any other data associated with system 600.

System 600 may further include user interface 609 for allowing an operator to adjust the various settings of system 600. In some embodiments, a user interface 609 may include a knob, slider, touch screen, keyboard, display, or any other interface component, or combinations thereof, to allow the operator to interact with system 600. For example, a knob or keyboard can be used to enter a selection of the energy value described above. This provides the user with an interface for easily and intuitively adjusting the amount of energy delivered to a patient by allowing system 600 to adjust the power and duration of the delivered laser treatment beam pulse. In some embodiments, user interface 609 may further provide a visible or audio cue to notify the user when to look for a visible lesion (e.g., 3 seconds or more after delivery of the laser treatment beam) when titrating the barely visible threshold value at block 501.

While specific components are shown in FIG. 6, it should be appreciated that system 600 may further include other components known to those of ordinary skill in the art, such as safety devices, hardware for aiming the laser treatment beam, or the like.

Various exemplary embodiments are described herein. Reference is made to these examples in a non-limiting sense. They are provided to illustrate more broadly applicable aspects of the disclosed technology. Various changes may be made and equivalents may be substituted without departing from the true spirit and scope of the various embodiments. In addition, many modifications may be made to adapt a particular situation, material, composition of matter, process, process act(s) or step(s) to the objective(s), spirit or scope of the various embodiments. Further, as will be appreciated by those with skill in the art that each of the individual variations described and illustrated herein has discrete components and features which may be readily separated from or combined with the features of any of the other several embodiments without departing from the scope or spirit of the various embodiments. All such modifications are intended to be within the scope of claims associated with this disclosure.

What is claimed is:

1. A method for laser treatment of an eye of a patient, the method comprising:
   receiving a laser treatment beam power and a laser treatment beam duration representing a dose of laser energy adapted to produce a first type of detectable lesion on the eye;
   determining a first Arrhenius integral value based on the received laser treatment beam power and laser treatment beam duration;
   determining a set of data points that define a first constant-Arrhenius curve corresponding to the first Arrhenius integral value,
      wherein the set of data points that define the first constant-Arrhenius curve represents combinations of laser treatment beam power and laser treatment beam duration adapted to produce the first type of detectable lesion;
   determining a set of data points that define a second constant-Arrhenius curve corresponding to a second Arrhenius integral value,
      wherein the second Arrhenius integral value has a logarithmic relationship to the first Arrhenius integral value,
      wherein the set of data points that define the second constant-Arrhenius curve represents combinations of laser treatment beam power and laser treatment beam duration adapted to produce a second type of detectable lesion, and
      wherein the first type and the second type of detectable lesion have different types of clinical results;
   determining a set of data points that define an operating curve for a laser treatment beam,
      wherein the operating curve intersects the first and second constant-Arrhenius curves, and wherein the set of data points that define the operating curve represents selectable combinations of laser treatment beam power and laser treatment beam duration configured to be output by a laser energy source for delivering doses of laser energy;

receiving a selection corresponding to a data point of the set of data points that define the operating curve;

in response to receiving the selection, adjusting at least one of a power and a duration of the laser treatment beam in accordance with the laser treatment beam power and the laser treatment beam duration represented by the selected data point of the operating curve; and outputting the laser treatment beam using the laser energy source.

2. The method of claim 1, wherein receiving the laser treatment beam power and the laser treatment beam duration representing a dose of laser energy adapted to produce the first type of detectable lesion comprises:

receiving selection of a maximum laser treatment beam duration; and adjusting the laser treatment beam power to a power adapted to produce the first type of detectable lesion when applied at the maximum laser treatment beam duration, wherein the maximum laser treatment beam duration and the adjusted laser treatment beam power are used to determine the first Arrhenius integral value.

3. The method of claim 1, wherein receiving the laser treatment beam power and the laser treatment beam duration representing a dose of laser energy adapted to produce the first type of detectable lesion comprises:

receiving selection of a maximum laser treatment beam power; and adjusting the laser treatment beam duration to a duration adapted to produce the first type of detectable lesion when applied at the maximum laser treatment beam power, wherein the maximum laser treatment beam power and the adjusted laser treatment beam duration are used to determine the first Arrhenius integral value.

4. The method of claim 1, wherein adjusting at least one of the power and the duration of the laser treatment beam comprises:

adjusting the power of the laser treatment beam, wherein the duration of the laser treatment beam is kept constant.

5. The method of claim 1, wherein adjusting at least one of the power and the duration of the laser treatment beam comprises:

adjusting the duration of the laser treatment beam, wherein the power of the laser treatment beam is kept constant.

6. The method of claim 1, further comprising:

receiving a selection of a laser treatment beam diameter; and in response to receiving the selection of the laser treatment beam diameter, adjusting the diameter of the laser treatment beam.

7. The method of claim 1, wherein the dose of laser energy adapted to produce the first type of detectable lesion represents a maximum energy value of the operating curve.

8. The method of claim 1, wherein the operating curve relates linear changes in energy value to exponential changes in Arrhenius integral values.

9. The method of claim 8, wherein receiving the selection corresponding to the data point of the set of data points that define the operating curve comprises:

receiving selection of a normalized energy value from a linear numerical scale of normalized energy values.

10. The method of claim 1, wherein at least one of the first type and the second type of detectable lesion is a sub-visible lesion.

11. A system for laser treatment of an eye of a patient, the system comprising:

a laser energy source configured to generate a laser treatment beam; and a computer processor configured to:

receive a laser treatment beam power and a laser treatment beam duration representing a dose of laser energy adapted to produce a first type of detectable lesion on the eye;

determine a first Arrhenius integral value based on the received laser treatment beam power and laser treatment beam duration;

determine a set of data points that define a first constant-Arrhenius curve corresponding to the first Arrhenius integral value, wherein the set of data points that define the first constant-Arrhenius curve represents combinations of laser treatment beam power and laser treatment beam duration adapted to produce the first type of detectable lesion;

determine a set of data points that define a second constant-Arrhenius curve corresponding to a second Arrhenius integral value, wherein the second Arrhenius integral value has a logarithmic relationship to the first Arrhenius integral value, wherein the set of data points that define the second constant-Arrhenius curve represents combinations of laser treatment beam power and laser treatment beam duration adapted to produce a second type of detectable lesion, and wherein the first type and the second type of detectable lesion have different types of clinical results;

determine a set of data points that define an operating curve for a laser treatment beam, wherein the operating curve intersects the first and second constant-Arrhenius curves, and wherein the set of data points that define the operating curve represents selectable combinations of laser treatment beam power and laser treatment beam duration configured to be output by a laser energy source for delivering doses of laser energy;

receive a selection corresponding to a data point of the set of data points that define the operating curve;

in response to receiving the selection, adjust at least one of a power and a duration of the laser treatment beam in accordance with the laser treatment beam power and the laser treatment beam duration represented by the selected data point of the operating curve; and output the laser treatment beam using the laser energy source.

12. The system of claim 11, wherein receiving the laser treatment beam power and the laser treatment beam duration representing a dose of laser energy adapted to produce the first type of detectable lesion comprises:

receiving selection of a maximum laser treatment beam duration; and adjusting the laser treatment beam power to a power adapted to produce the first type of detectable lesion when applied at the maximum laser treatment beam duration,
wherein the maximum laser treatment beam duration and the adjusted laser treatment beam power are used to determine the first Arrhenius integral value.

13. The system of claim 11, wherein receiving the laser treatment beam power and the laser treatment beam duration representing a dose of laser energy adapted to produce the first type of detectable lesion comprises:
receiving selection of a maximum laser treatment beam power; and
adjusting the laser treatment beam duration to a duration adapted to produce the first type of detectable lesion when applied at the maximum laser treatment beam power,
wherein the maximum laser treatment beam power and the adjusted laser treatment beam duration are used to determine the first Arrhenius integral value.

14. The system of claim 11, wherein adjusting at least one of the power and the duration of the laser treatment beam comprises:
adjusting the power of the laser treatment beam, wherein the duration of the laser treatment beam is kept constant.

15. The system of claim 11, wherein adjusting at least one of the power and the duration of the laser treatment beam comprises:
adjusting the duration of the laser treatment beam, wherein the power of the laser treatment beam is kept constant.

16. The system of claim 11, wherein the computer processor is further configured to:
receive a selection of a laser treatment beam diameter; and
in response to receiving the selection of the laser treatment beam diameter, adjust the diameter of the laser treatment beam.

17. The system of claim 11, wherein the dose of laser energy adapted to produce the first type of detectable lesion represents a maximum energy value of the operating curve.

18. The system of claim 11, wherein the operating curve relates linear changes in energy value to exponential changes in Arrhenius integral values.

19. The system of claim 18, wherein receiving the selection corresponding to the data point of the set of data points that define the operating curve comprises:
receiving selection of a normalized energy value from a linear numerical scale of normalized energy values.

20. The system of claim 11, wherein at least one of the first type and the second type of detectable lesion is a sub-visible lesion.

21. A non-transitory computer-readable storage medium having computer-executable instructions for treating an eye of a patient using a laser treatment beam, the computer-executable instructions comprising instructions for:
receiving a laser treatment beam power and a laser treatment beam duration representing a dose of laser energy adapted to produce a first type of detectable lesion on the eye;
determining a first Arrhenius integral value based on the received laser treatment beam power and laser treatment beam duration;
determining a set of data points that define a first constant-Arrhenius curve corresponding to the first Arrhenius integral value,
wherein the set of data points that define the first constant-Arrhenius curve represents combinations of laser treatment beam power and laser treatment beam duration adapted to produce the first type of detectable lesion;
determining a set of data points that define a second constant-Arrhenius curve corresponding to a second Arrhenius integral value,
wherein the second Arrhenius integral value has a logarithmic relationship to the first Arrhenius integral value,
wherein the set of data points that define the second constant-Arrhenius curve represents combinations of laser treatment beam power and laser treatment beam duration adapted to produce a second type of detectable lesion, and
wherein the first type and the second type of detectable lesion have different types of clinical results;
determining a set of data points that define an operating curve for a laser treatment beam,
wherein the operating curve intersects the first and second constant-Arrhenius curves, and
wherein the set of data points that define the operating curve represents selectable combinations of laser treatment beam power and laser treatment beam duration configured to be output by a laser energy source for delivering doses of laser energy;
receiving a selection corresponding to a data point of the set of data points that define the operating curve;
in response to receiving the selection, adjusting at least one of a power and a duration of the laser treatment beam in accordance with the laser treatment beam power and the laser treatment beam duration represented by the selected data point of the operating curve; and
outputting the laser treatment beam using the laser energy source.

22. The non-transitory computer-readable storage medium of claim 21, wherein receiving the laser treatment beam power and the laser treatment beam duration representing a dose of laser energy adapted to produce the first type of detectable lesion comprises:
receiving selection of a maximum laser treatment beam duration; and
adjusting the laser treatment beam power to a power adapted to produce the first type of detectable lesion when applied at the maximum laser treatment beam duration,
wherein the maximum laser treatment beam duration and the adjusted laser treatment beam power are used to determine the first Arrhenius integral value.

23. The non-transitory computer-readable storage medium of claim 21, wherein receiving the laser treatment beam power and the laser treatment beam duration representing a dose of laser energy adapted to produce the first type of detectable lesion comprises:
receiving selection of a maximum laser treatment beam power; and
adjusting the laser treatment beam duration to a duration adapted to produce the first type of detectable lesion when applied at the maximum laser treatment beam power,
wherein the maximum laser treatment beam power and the adjusted laser treatment beam duration are used to determine the first Arrhenius integral value.

24. The non-transitory computer-readable storage medium of claim 21, wherein adjusting at least one of the power and the duration of the laser treatment beam comprises:

adjusting the power of the laser treatment beam, wherein the duration of the laser treatment beam is kept constant.

25. The non-transitory computer-readable storage medium of claim 21, wherein adjusting at least one of the power and the duration of the laser treatment beam comprises:

adjusting the duration of the laser treatment beam, wherein the power of the laser treatment beam is kept constant.

26. The non-transitory computer-readable storage medium of claim 21, further comprising instructions for:

receiving a selection of a laser treatment beam diameter; and in response to receiving the selection of the laser treatment beam diameter, adjusting the diameter of the laser treatment beam.

27. The non-transitory computer-readable storage medium of claim 21, wherein the dose of laser energy adapted to produce the first type of detectable lesion represents a maximum energy value of the operating curve.

28. The non-transitory computer-readable storage medium of claim 21, wherein the operating curve relates linear changes in energy value to exponential changes in Arrhenius integral values.

29. The non-transitory computer-readable storage medium of claim 28, wherein receiving the selection corresponding to the data point of the set of data points that define the operating curve comprises:

receiving selection of a normalized energy value from a linear numerical scale of normalized energy values.

30. The non-transitory computer-readable storage medium of claim 21, wherein at least one of the first type and the second type of detectable lesion is a sub-visible lesion.

* * * * *